(12) United States Patent
Schabbach

(10) Patent No.: US 7,922,974 B2
(45) Date of Patent: Apr. 12, 2011

(54) HANDHELD APPARATUS FOR ANALYSIS WITH A CONVEYANCE PATH FOR TEST ELEMENTS

(75) Inventor: Michael Schabbach, Weinheim (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 633 days.

(21) Appl. No.: 10/591,311

(22) PCT Filed: Feb. 5, 2005

(86) PCT No.: PCT/EP2005/001196
§ 371 (c)(1), (2), (4) Date: Sep. 1, 2006

(87) PCT Pub. No.: WO2005/085840
PCT Pub. Date: Sep. 15, 2005

(65) Prior Publication Data
US 2007/0183925 A1 Aug. 9, 2007

(30) Foreign Application Priority Data
Mar. 4, 2004 (DE) .......................... 10 2004 010 529

(51) Int. Cl.
*G01N 33/00* (2006.01)
(52) U.S. Cl. ................ 422/61; 422/50; 422/55; 422/56; 422/58; 422/68.1
(58) Field of Classification Search ............... 422/55, 422/58, 61, 68.1, 99, 104, 50, 56
See application file for complete search history.

(56) References Cited

U.S. PATENT DOCUMENTS

| | | | |
|---|---|---|---|
| 3,918,910 A | 11/1975 | Soya et al. | |
| 4,065,263 A | 12/1977 | Woodbridge, III | |
| 4,302,420 A | 11/1981 | Jakubowicz et al. | |
| 4,432,567 A | 2/1984 | Stockburger et al. | |
| 4,710,352 A | 12/1987 | Slater et al. | |
| 4,791,461 A | 12/1988 | Kishimoto et al. | |
| 4,833,088 A | 5/1989 | DeSimone et al. | |
| 4,857,471 A | 8/1989 | Salzman et al. | |
| 4,876,204 A | 10/1989 | Inoue et al. | |
| 5,073,342 A | 12/1991 | Porte et al. | |
| 5,097,938 A | 3/1992 | Gruner et al. | |
| 5,236,078 A | 8/1993 | Gross et al. | |

(Continued)

FOREIGN PATENT DOCUMENTS

DE 24 07 320 * 8/1975

(Continued)

OTHER PUBLICATIONS

PCT English translation of the International Preliminary Report dated Nov. 15, 2006, regarding PCT/EP2005/001196 (8 pages).

*Primary Examiner* — Sam P Siefke
(74) *Attorney, Agent, or Firm* — Barnes & Thornburg LLP

(57) ABSTRACT

A handheld device for analyzing a sample for a medically significant component may comprise an analysis sensor to which an analytic consumable may be supplied along a conveyance path, a drivable conveyance roll configured to grip the analytic consumable protruding into the conveyance path, a motor configure to drive the drivable conveyance roll, and a housing containing the analysis sensor, the drivable conveyance roll and the motor.

22 Claims, 5 Drawing Sheets

U.S. PATENT DOCUMENTS

| | | | |
|---|---|---|---|
| 5,415,840 | A | 5/1995 | Sano et al. |
| 5,505,308 | A | 4/1996 | Eikmeier et al. |
| 5,510,266 | A | 4/1996 | Bonner et al. |
| 5,575,403 | A | 11/1996 | Charlton et al. |
| 5,686,047 | A | 11/1997 | Augstein |
| 6,475,436 | B1 | 11/2002 | Schabbach et al. |
| 6,497,845 | B1 | 12/2002 | Sacherer |
| 6,534,017 | B1 * | 3/2003 | Bottwein et al. |
| 2002/0057993 | A1 * | 5/2002 | Maisey et al. |
| 2003/0049849 | A1 * | 3/2003 | Mori et al. |
| 2003/0212344 | A1 * | 11/2003 | Yuzhakov et al. |
| 2005/0163661 | A1 * | 7/2005 | Ziegler |

FOREIGN PATENT DOCUMENTS

| | | |
|---|---|---|
| DE | 198 19 407 | * 11/1999 |
| EP | 1022565 | 7/2000 |
| WO | 9746887 | 12/1997 |

* cited by examiner

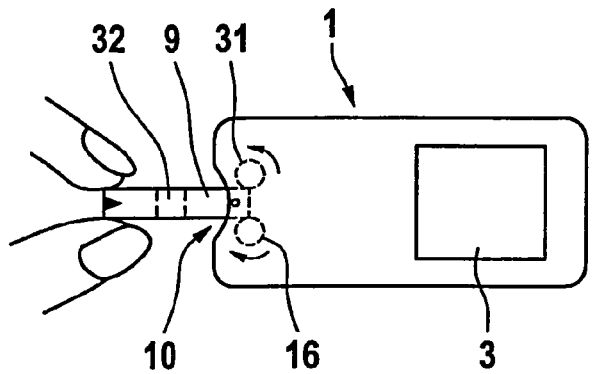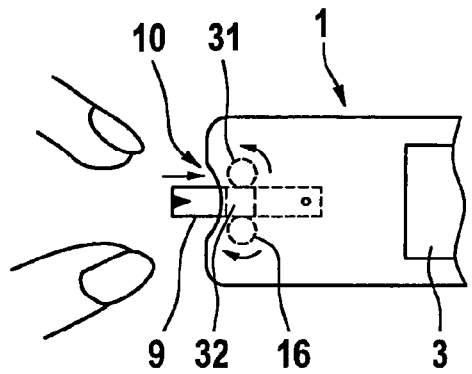
Fig. 8        Fig. 9
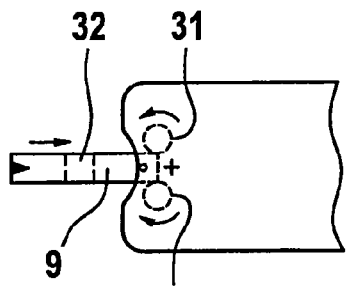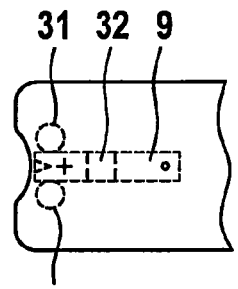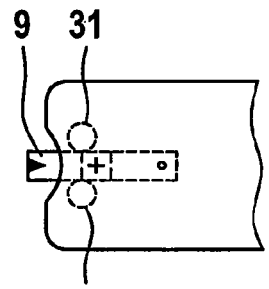
Fig. 10        Fig. 11        Fig. 12
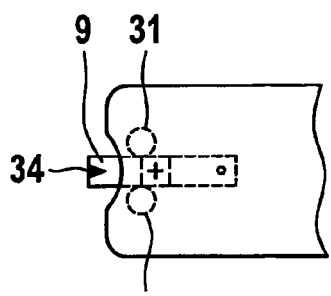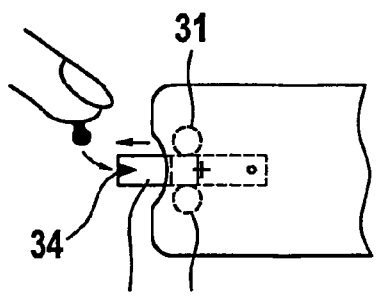
Fig. 13        Fig. 14

HANDHELD APPARATUS FOR ANALYSIS WITH A CONVEYANCE PATH FOR TEST ELEMENTS

CROSS-REFERENCE TO RELATED APPLICATIONS

This application is a U.S. national counterpart application of international application serial no. PCT/EP2005/001196 filed Feb. 5, 2005, which claims priority to German application serial no. 10 2004 010 529.4 filed Mar. 4, 2004.

FIELD OF THE INVENTION

The present invention relates generally to a handheld analysis device for analyzing a sample, in particular a biological liquid, for a medically significant component, and more specifically to such a handheld analysis device comprising an analysis sensor to which an analytic consumable may be supplied along a conveyance path.

BACKGROUND

Carriers for rapid tests have become established for chemical and biochemical analysis of solid and liquid sample materials in laboratories specialized for this purpose and, in particular, also for use outside stationary laboratories. Such carrier-bound rapid tests may be performed easily and straightforwardly even by laymen despite the often complex reactions involving sensitive reagents.

Test elements for determining the blood glucose level of diabetics are a known example of carrier-bound rapid tests. Diagnostic test elements provided in the form of strips are also called to as test strips. Known embodiments thereof include, for example, single-field or multiple-field test strips for urine analysis and various indicator papers. Since various forms of test elements other than test strips exist, test elements are more generally denoted as "analytic consumables", which also include lancets or sample removal elements, for example.

Analytic consumables of this type are used in a portable handheld analysis device which analyzes a coloration of a test strip photometrically using an optical analysis sensor, for example. The analytic consumables may be stored in a drum magazine, as is described, for example, in EP 1 022 565 A2. The drum magazine described therein comprises multiple chambers arranged annularly, which can contain analytic consumables. Each chamber has a removal opening on a front face of the drum magazine. These removal openings are typically sealed by sealing foil, in order to protect the analytic consumables from detrimental environmental influences, such as moisture, light, or dust.

Handheld analysis devices for analyzing a medically significant component of a sample, such as devices for blood glucose monitoring, are typically used multiple times a day and carried continuously by a user. Therefore, it is desirable to provide small handheld analysis devices that are simultaneously easy to handle.

SUMMARY

The present invention may comprise one or more of the features recited in the attached claims, and/or one or more of the following features and combinations thereof.

In a handheld analysis device according to the present disclosure an analytic consumable, to which a drop of blood or urine was applied, for example, may be supplied by a conveyance roll to the analysis sensor in the interior of the device with precision.

The handheld analysis device preferably has a switch which is actuated upon insertion of a consumable into the housing opening and turns on a drive of the conveyance roll. Such a switch may be a mechanical switch, for example, which is triggered by a small rotational movement of the conveyance roll, which is caused by pressure of an inserted consumable against the conveyance roll. The switch may be implemented as a light barrier, for example. A further possibility is to implement the switch as two contact fields which are arranged at a distance from one another and brought into electrical contact by a consumable inserted into the conveyance opening. Even a very slight change of the electrical resistance between the two contact fields, as is caused by an inserted consumable made of plastic or paper, for example, may be reliably detected by a suitable transistor circuit.

In a handheld analysis device according to the present disclosure, the user only has to insert one end of the consumable lightly into the housing opening. The conveyance roll then grips the consumable. The transport of the consumable and its correct positioning with respect to the analysis sensor is performed automatically. A final position of the consumable may be detected mechanically, electrochemically, or optically using, for example, a position switch, which then turns off the drive of the conveyance roll. The removal facility may be implemented compactly. Hence, a handheld analysis device may be made small, particularly if a drum magazine is used. Known handheld analysis devices having a removal facility for a drum magazine according to EP 1 022 565 A2 require a pushrod of significant length implemented as a plunger, which is inserted for removal of a consumable into an insertion opening of a chamber of the drum magazine. The insertion opening is diametrically opposite of a removal opening. Thus a consumable contained in the chamber is pushed out of the chamber and a housing opening of the device. For a pushrod to fulfill this purpose, it must have a length which at least corresponds to the length of the path on which a consumable is transported upon removal.

The pushrod and the housing of the handheld analysis device disclosed herein may be constructed compactly. In a handheld analysis device according to the present disclosure it is sufficient if a consumable can be pushed by a pushrod just far out of the chamber that it may be gripped by the conveyance roll and moved in the removal direction. The conveyance roll is situated directly adjacent to the removal opening of the inserted drum magazine, so that it is sufficient if the consumable is pushed approximately 0.5 to 1 cm out of its chamber by the pushrod. For this purpose, a pushrod having a length of 1 to 2 cm is sufficient.

Using the conveyance roll, a consumable may be pushed far enough out of a housing opening of the housing so that a sample, such as a drop of blood, may be applied to the consumable without a risk of contamination of the handheld analysis device by the sample.

BRIEF DESCRIPTION OF THE DRAWINGS

Further details and advantages of the present invention will be explained on the basis of exemplary embodiments with reference to the attached figures. Identical and corresponding parts are identified by identical reference numerals. The special features shown therein may be used individually or in combination to provide preferred embodiments of the present invention. In the Figures:

FIGS. 8 through 14 show a further exemplary embodiment of a handheld analysis device during insertion of a consumable.

DESCRIPTION OF THE ILLUSTRATIVE EMBODIMENTS

For the purposes of promoting an understanding of the principles of the invention, reference will now be made to a number of illustrative embodiments shown in the attached drawings and specific language will be used to describe the same.

Figure 1:
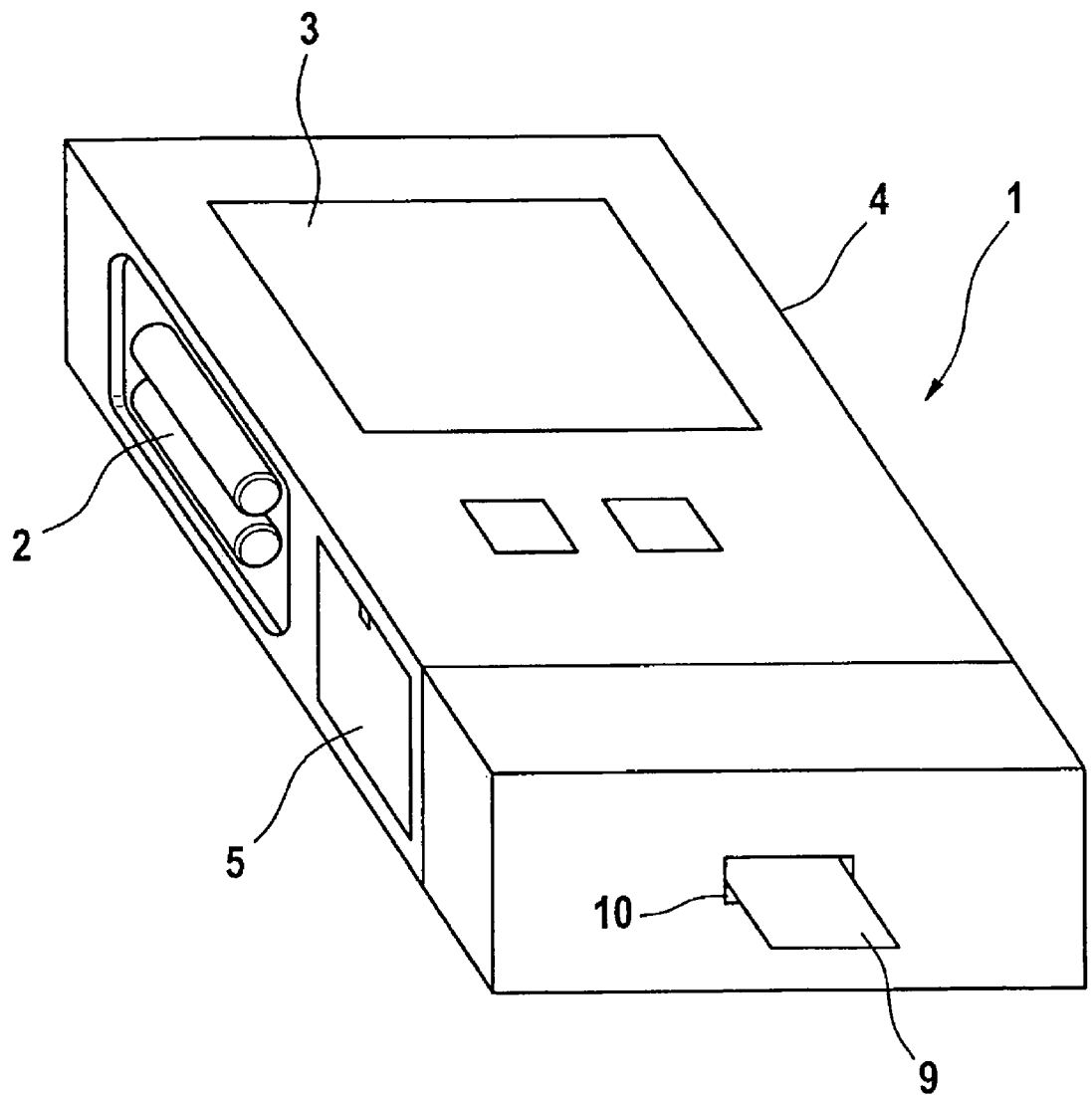
FIG. 1 shows an embodiment of a handheld analysis device.

FIG. 1 shows a compact, portable handheld analysis device 1 for analyzing a sample, particularly a biological liquid, for a medically significant component such as blood, urine or saliva. The handheld analysis device 1 shown in FIG. 1 is used for determining the concentration of glucose in blood and has a power source 2 in the form of commercially available batteries or solar cells. The result of an analysis is displayed by a display unit 3, preferably a liquid crystal display. The handheld analysis device 1 comprises a housing 4, which has a loading opening 5 for receiving a replaceable drum magazine 6 in a magazine compartment 7. The drum magazine 6 is rotatable in the magazine compartment 7 step-by-step around its geometrical longitudinal axis by an electric motor 8, so that analytic consumables 9 stored in the drum magazine 6 may be removed through a housing opening 10 of the housing 4.

The generally cylindrical drum magazine 6 has multiple chambers 11 that are disposed in a ring-shaped arrangement around its geometrical longitudinal axis and can contain analytic consumables 9. The number of chambers 11 may be varied arbitrarily to a large extent. Typically, 10 to 100 chambers 11 are expedient, 15 to 30 chambers 11 are preferably provided. Each of the chambers 11 has a removal opening 12 on a front face of the drum magazine 6 for removing a consumable 9 and an insertion opening 13 diametrically opposite the removal opening 12 for inserting a plunger 14 of a removal facility 29. The insertion openings 12 and the removal openings 13 are sealed by a sealing foil to protect the consumables 9 from detrimental environmental influences. As described in EP 1 022 565 A2, consumables 9 to be used may be pushed out of the chambers 11 by the pushrod 14 implemented as a plunger. The sealing foil of the insertion opening 13 is thereby penetrated by the plunger 14 and the sealing foil of the removal opening 12 penetrated by the consumable 9.

The consumables 9 are preferably test strips, to which a sample may be applied. A reagent contained in the test strips reacts with a medically significant component of the sample, so that the result of the reaction may be analyzed using an analysis sensor 15 of the handheld analysis device 1. Such an analysis sensor 15 may be an optical sensor, for example, which detects a color change of a consumable 9 provided as a test strip, or it may be an electrical sensor which detects a conductivity change of the sample.

Figure 2:
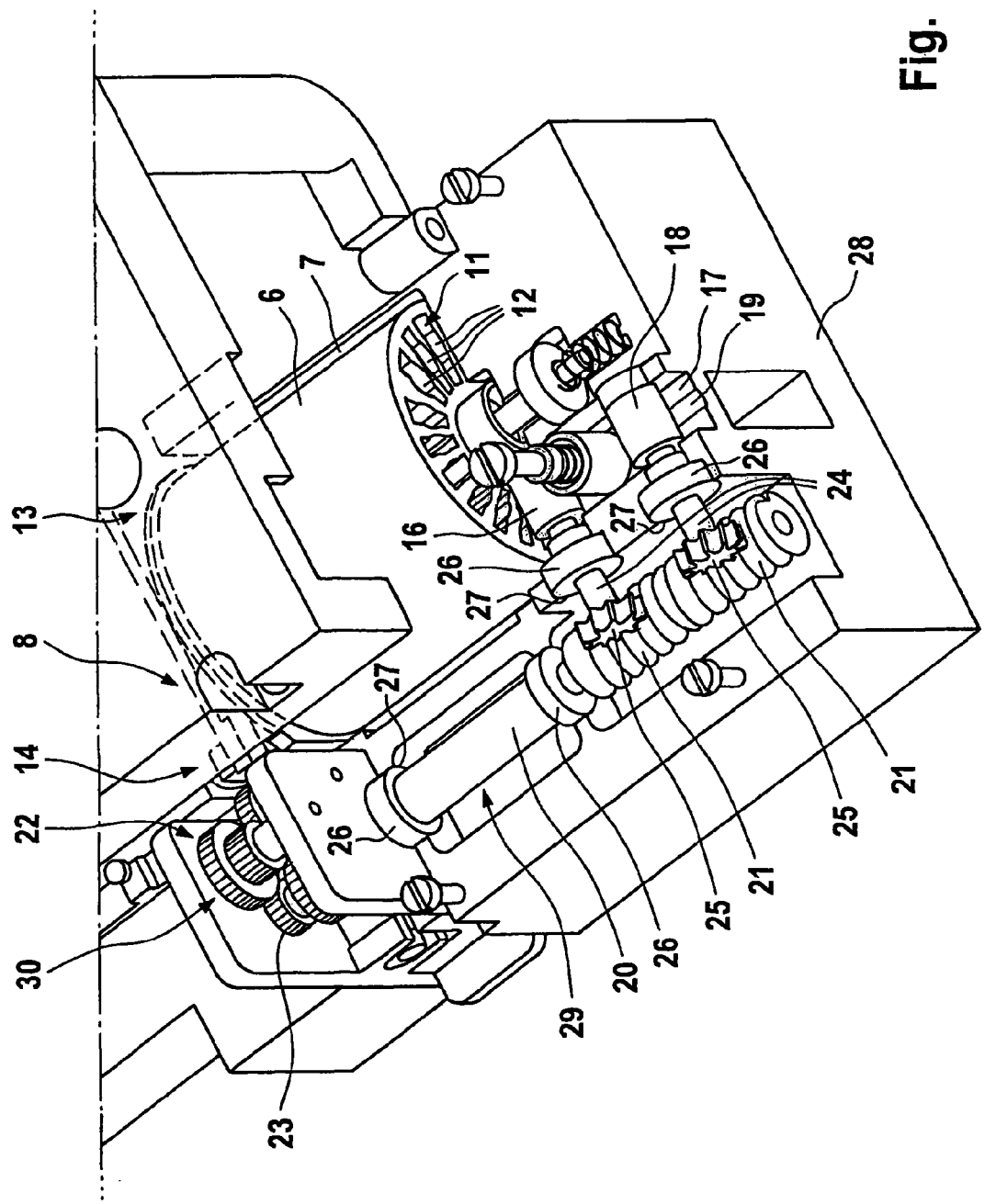
FIG. 2 shows an embodiment of a removal facility of the handheld analysis device shown.

The drum magazine 6 may be rotated step-by-step by the electric motor 8, so that one after another each of the removal openings 12 can be aligned with the housing opening 10 of the housing 4 and then a consumable 9 pushed out of the chamber 11, which is currently positioned for removal, by the plunger 14 of the removal facility 29. The removal facility 29 comprises a drivable conveyance roll 16, shown in FIG. 2, in addition to the plunger 14. The conveyance roll 16 may grip a consumable 9 protruding out of the drum magazine 6 and move it entirely or partially out of the drum magazine in the removal direction. The conveyance roll 16 therefore allows the plunger 14 to be relatively short since it is sufficient if the consumable 9 may be pushed a small amount out of the chamber 11 by the plunger 14.

The conveyance roll 16 is illustratively situated directly adjacent to the removal opening 12 of the inserted drum magazine 6. In this way a consumable 9 has to protrude only slightly out of its chamber 11 to be able to be gripped by the conveyance roll 16. In this way only a small minimum distance of approximately 1 mm is required between the front face of the inserted drum magazine 6 and the conveyance roll 16, so that the conveyance roll 16 and the inserted drum magazine 6 may rotate undisturbed. As a further measure for gripping a consumable 9 closely to the removal opening 12 by the conveyance roll 16 and thus for making the plunger 14 as relatively short, the conveyance roll 16 illustratively has a small diameter of approximately 3 to 10 mm, of and in some embodiments 4 to 7 mm.

The conveyance roll 16 and a conveyance surface, which is stationary in relation thereto, form together a conveyance gap, through which the consumable 9 is moved in the conveyance direction. Alternatively, the conveyance roll 16 may—as shown in FIGS. 3 to 7—form a conveyance gap together with a counter roll 31 situated diametrically opposite thereto. The conveyance gap illustratively has a profile tailored to the consumable 9, in the form of a groove in the conveyance surface or the counter roll, for example, so that a test field of the consumable 9 is not squeezed and thus impaired during removal. In the embodiment shown in FIG. 2, the conveyance roll 16 works together with a stationary conveyance surface.

The handheld analysis device 1 has a conveyance base 17 extending in the removal direction to support a removed consumable 9. The conveyance surface, which forms the conveyance gap 33 together with the conveyance roll 16, is part of the conveyance base 17 extending from the magazine compartment 7 to the housing opening 10. In this way, a removed consumable 9 is supported and guided on its entire conveyance path by the conveyance base 17.

A further conveyance roll 18, which forms a second conveyance gap together with the conveyance base 17, is situated at a distance from the conveyance roll 16 in the conveyance direction. While the first conveyance roll 16 is arranged as close as possible to the removal opening 12 of an inserted drum magazine 6 so that a consumable 9 has to protrude as little as possible out of its chamber 11 to be able to be gripped, the second conveyance roll 18 is situated as close as possible to the housing opening 10 of the housing 4, so that a consumable 9 may be pushed as far as possible out of the housing opening 10 of the housing 4. The further a consumable 9, e.g. in the form of a test strip, may be pushed out of the housing opening 10 of the housing 4, the easier may a sample, such as a drop of blood, be applied to the consumable 9 without contaminating the housing 4.

The conveyance base 17 is provided with a groove 19 running in the conveyance direction. This minimizes friction between the consumable 9 and the conveyance base 17. While the conveyance base 17 is manufactured from a material which is smooth and has a low coefficient of friction, such as polycarbonate, the conveyance rolls 16, 18 illustratively have a surface configured to have a high coefficient of friction. For example, the rolls may have a roughened surface, may be made of hard or soft rubber, or may be coated with a rubber-like plastic to increase the friction. If the consumable 9 has a thickness varying over its length, the conveyance roll may be spring-loaded to adapt to differences in thickness.

In the embodiment shown, the conveyance rolls 16, 18 and the plunger 14 of the removal facility 29 are moved by a single drive 30. Alternatively, it is also possible to provide separate micromotors as drives for the plunger 14 and the conveyance rolls 16, 18 or even for each of the conveyance rolls 16, 18. However, it is more cost-effective and therefore preferable if the removal facility 29 only has one drive 30, which drives both the conveyance rolls 16, 18 and also the plunger 14.

In order to be able to transmit movement generated by the joint drive 30 of the removal facility 29 both to the plunger 14 and the conveyance rolls 16, 18, the removal facility 29 comprises a threaded rod 20 having a thread 21. The rod 20 extends laterally along the inserted drum magazine 6 and projects on both sides beyond its front faces. In the embodiment shown in FIG. 2, the removal facility 29 has a transmission 22, via which an electric motor belonging to the drive 30 may move the plunger 14. The threaded rod 20 comprises a gearwheel 23 which works together with the transmission 22, so that the threaded rod 20 may be set into rotation via the transmission 22 and the gearwheel 23. The gearwheel 23 may be a separate component which is attached to the threaded rod 20, or may be integrated in the threaded rod 20, by providing a section of the threaded rod 20 with teeth, for example. In the illustrated embodiment, the gearwheel 23 is illustratively situated on or near an end of the threaded rod 20 and the thread 21 is preferably situated on or near the other end.

A rotation of the threaded rod 20 is transmittable to the conveyance rolls 16, 18 via the external thread 21 situated on the other end of the threaded rod 20. For this purpose, each of the two conveyance rolls 16, 18 is provided with a shaft 24 which carries a gearwheel 25 which engages in the thread 21 of the threaded rod 20. The shaft 24 and the threaded rod 20 are mounted using bearing rings 26, which lie rotatably with little frictional resistance in fitted recesses 27 of the carrier 28.

The conveyance rolls 16, 18 are preferably drivable around their geometrical longitudinal axes both clockwise and also counterclockwise in order to be able to move a consumable 9 both in the removal direction and also in the opposite direction. This measure allows a consumable 9, such as a test strip, to be pushed as far as possible out of the opening 10 of the housing 4, in order to facilitate applying a sample, and to subsequently retract the consumable 9 back into the handheld analysis device 1. It is thus possible to situate the analysis sensor 15 at a protected location in the interior of the housing 4, where interfering environmental influences, such as stray light, are minimized. The analysis sensor 15 is preferably situated between the two conveyance rolls 16, 18, in particular on the side of the conveyance base 17 diametrically opposite of the conveyance rolls 16, 18. The conveyance base 17 is provided with a recess between the two conveyance rolls 16, 18, so that the analysis sensor 15 may detect a sample applied to a consumable 9. The groove 19 of the conveyance base 17 running in the conveyance direction has its width and depth dimensioned in such a manner that a sample applied to the consumable 9 does not come into contact with the conveyance base 17.

If the conveyance rolls 16, 18 are rotatable around their geometrical longitudinal axes both clockwise and also counterclockwise, so that the consumable 9 may be moved both in the removal direction and also in the opposite direction, it is possible to reinsert a used consumable 9 into its chamber 11 of the drum magazine 6 after analysis is completed. In order to facilitate returning of a used consumable 9 to the magazine, the plunger 14 is equipped with a gripper element which may operationally engage a consumable 9 and allows a consumable 9 to be pulled by the plunger 14 as well. For example, the gripper element may comprise an electromagnet which attracts an iron part of the consumable, or a mechanical hook which turns over at a predefined tensile force, as is exerted by the conveyance rolls 16, and releases the consumable 9.

In this way all consumables 9 contained in a drum magazine 6 may be disposed of together and a user no longer needs to dispose of a used consumable 9 individually after each analysis.

FIGS. 3 through 7 show a schematic illustration of a further exemplary embodiment of a removal facility during removal of a consumable 9 from a drum magazine 6. In contrast to the embodiment described above, in the removal facility 29 shown in FIGS. 3 through 7, the conveyance gap 33 is not provided by the conveyance rolls 16 and a conveyance surface stationary in relation thereto, but rather by the conveyance roll 16 and a counter roll 31 situated diametrically opposite thereto. In the embodiment shown in FIGS. 3 through 7, both the conveyance roll 16 and also the counter roll 31 may each be implemented as drivable. However, it is sufficient if only the conveyance roll 16 is drivable. For the counter roll 31, it is sufficient if it is mounted in a rotatable way, so that it may be set into rotation by a consumable 9 passing through the conveyance gap 33.

In the embodiment shown in FIGS. 3 through 7, the consumables 9 are test strips which have a test field 32 for receiving a sample. To prevent impairment of the test field 32 during removal of the consumable 9 from the drum magazine 6 and to prevent contamination of the removal facility 29, particularly the conveyance roll 16 and the counter roll 31, by the consumable 9, the consumable 9 passes through the conveyance gap in such a manner that the test field 32 of the consumable 9 extends transversely to the geometric axis of rotation of the conveyance roll 16 in the embodiment shown. In this way, the danger of impairing the test field 32 of the consumable 9 is reduced by a conveyance gap 33 having a profile, which is tailored to the consumable 9 and has the form of a groove 19 in the conveyance base 17 providing the conveyance surface, for example.

Figure 3:
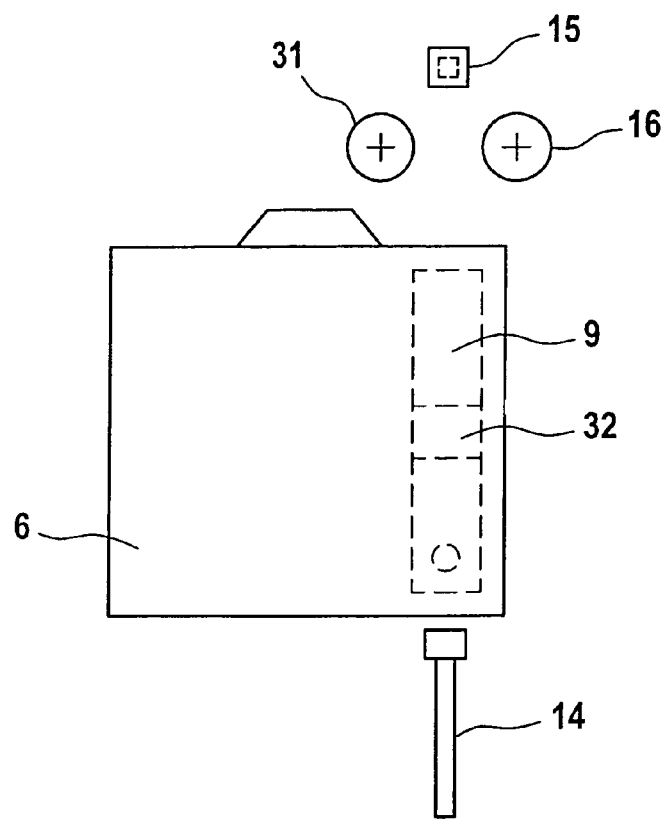
FIGS. 3 through 7 show a further exemplary embodiment of a removal facility during removal of a consumable.
Figure 4:
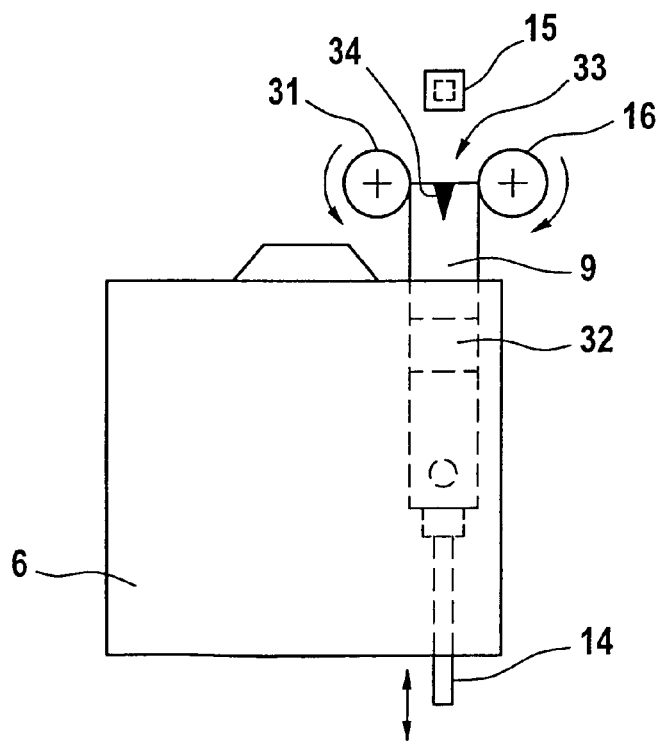
Figure 5:
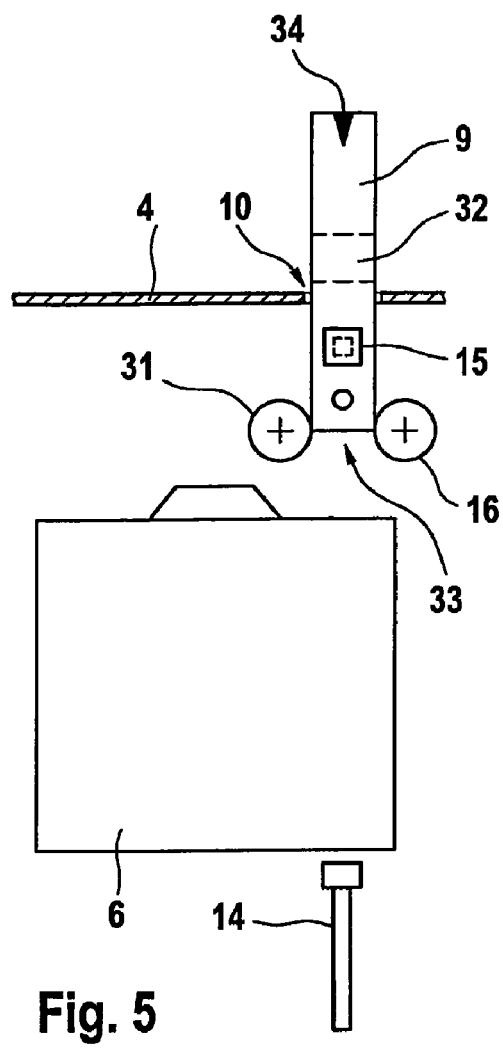
Figure 6:
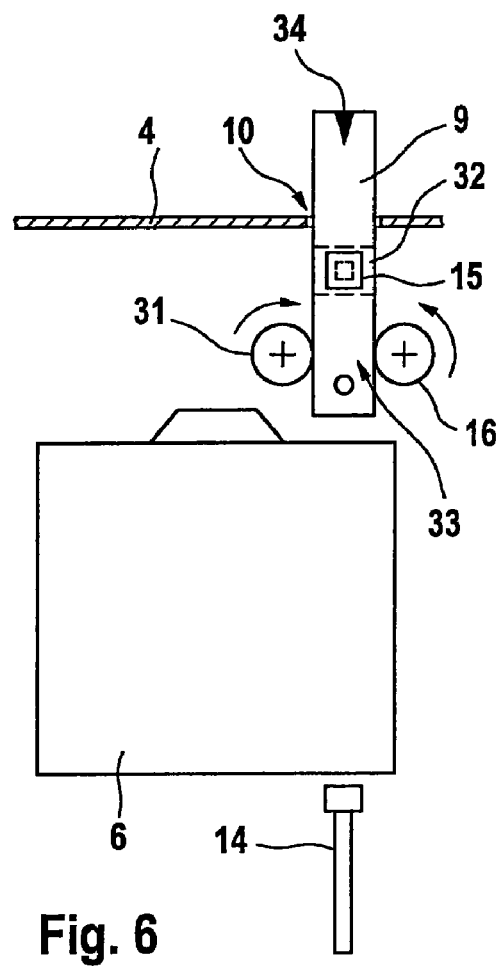
Figure 7:
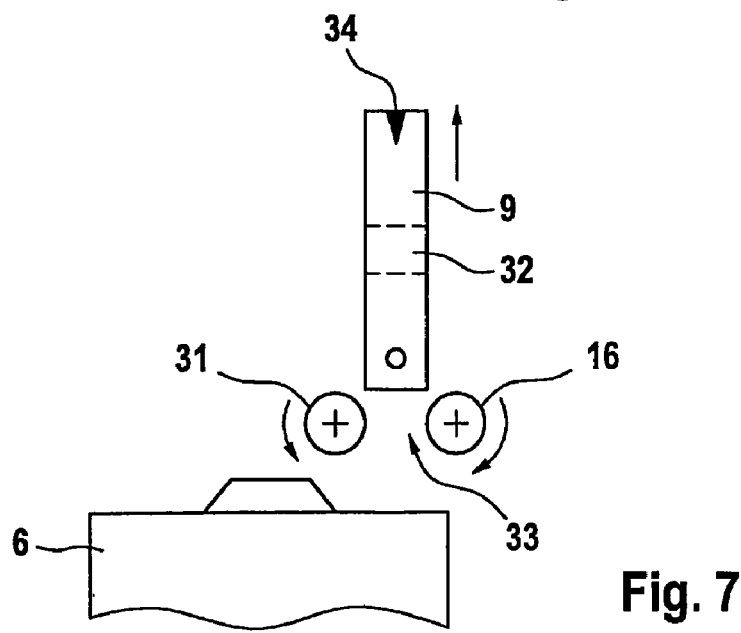

FIG. 3 shows the drum magazine 6 and a consumable 9 contained therein together with the removal facility 29 in the starting position. As may be seen in FIG. 4, the consumable 9 is pushed out of the drum magazine 6 by the plunger 14 and gripped by the conveyance roll 16 as soon as it protrudes into the conveyance gap 33 between the conveyance roll 16 and the counter roll 31. FIG. 5 shows how the consumable 9 is pushed out of the housing opening 10 of the handheld analysis device 1 by the conveyance roll 16, so that a sample, such as a drop of blood, may be applied to a sample application surface 34, from which it reaches the test field 32. Subsequently, as shown in FIG. 6, the consumable 9 is retracted back into the handheld analysis device 1 by the conveyance roll 16, which now rotates in the opposite direction, so that the test field 32 is positioned in front of the analysis sensor 15 for the analysis of the sample. After the plunger 14 has pushed the consumable 9 out of the drum magazine 6, it returns into its starting position shown in FIG. 6. After completion of the analysis, the consumable 9 is moved back in the removal direction by the conveyance roll 16 and ejected from the handheld analysis device 1, as shown in FIG. 7.

FIGS. 8 through 14 show a further embodiment of a handheld analysis device 1 during insertion of a consumable 9. This handheld analysis device 1 differs from the handheld analysis device 1 described above essentially in that it does not have a loading opening for receiving a replaceable drum magazine. In the handheld analysis device 1 shown in FIGS. 8 through 14, analytic consumables 9 in the form of test strips are therefore supplied to the device externally through the housing opening 10. By insertion of a consumable 9 into the housing opening 10, a microswitch (not shown) is actuated, through which a drive of the conveyance roll 16 and the counter roll 31 is turned on. As shown in FIG. 9, the consumable 9 is then gripped by the conveyance roll 16 and the counter roll 31 and drawn along the conveyance path into the device interior.

If the analytic consumables 9, as in the embodiment shown, are not removed from a drum magazine 6 loaded into the handheld analysis device 1, but rather supplied externally, there is increased danger that the consumables 9 have been spoiled by aging or detrimental environmental influences, such as light, moisture, or dust. A consumable 9 is therefore first conveyed from the insertion position shown in FIG. 10 into the test position shown in FIG. 11, in which it is checked whether it is spoiled. This is done by an optical measuring unit, by which a film white level of the consumable 9 is determined. For this purpose a consumable 9 provided as a test strip has a section having a white plastic film, which discolors with increasing age and moisture absorption and may be arranged in the area of the test field 32, for example. By determining the film white level, it may be established whether the inserted consumable 9 is spoiled. If a consumable 9 is spoiled, it is ejected from the handheld analysis device 1 using the conveyance roll 16 and the counter roll 31. If the consumable 9 is still functional, it is brought by the conveyance roll 16 and the counter roll 31 along the conveyance path into the sample application position shown in FIG. 14. In the sample application position, one end of the consumable 9 protrudes out of the housing opening 10, so that a sample, such as a blood drop, may be applied to the sample application surface 34.

The consumable 9 may protrude far enough out of the housing opening 10 in the sample application position shown in FIG. 14 that a sample may be applied easily to the sample application surface 34 without thereby contaminating the handheld analysis device 1. A consumable 9 protruding relatively far out of the housing opening 10 in the sample application position, reveals more easily to a user that a sample is now to be applied to the sample application surface 34. In particular, the test field 32, to which the sample is supplied by capillary forces, for example, may be situated so close to the sample application surface 34 that the required sample volume is minimal.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected.

The invention claimed is:

1. A handheld analysis device for analyzing a sample for a medically significant component, comprising:
    an analysis sensor to which an analytic consumable may be supplied along a conveyance path,
    a movable magazine having a chamber containing the analytic consumable, the chamber having an opening through which the analytic consumable may pass to the conveyance path,
    a movable pushrod extending, when moved, into the chamber and pushing the analytic consumable through the chamber opening at least partially into the conveyance path,
    a first motor, separate from the movable pushrod, which drives movement of the magazine, and
    a drivable conveyance roll which, when driven, transports along the conveyance path the analytic consumable pushed by the pushrod at least partially into the conveyance path.

2. The handheld analysis device of claim 1 wherein the drivable conveyance roll automatically grips, when driven, the analytic consumable and advances the automatically gripped analytic consumable along the conveyance path.

3. The handheld analysis sensor of claim 1 further comprising a housing containing the analysis sensor, the magazine, the first motor, the pushrod and the drivable conveyance roll, the housing defining an opening through which the analytic consumable may pass, the conveyance path following on the housing opening.

4. The handheld analysis device of claim 1 further comprising a second motor that drives the drivable conveyance roll, the second motor contained within the housing.

5. The handheld analysis device of claim 4 wherein the second motor is configured to drive the drivable conveyance roll in a first direction that moves the gripped analytic consumable along the conveyance path in a direction toward the housing opening, and to also drive the drivable conveyance roll in a second direction that moves the gripped analytic consumable long the conveyance path in a direction away from the housing opening.

6. The handheld analysis device of claim 3 wherein the movable magazine comprises defining the chamber containing the analytic consumable therein.

7. The handheld analysis device of claim 6 wherein the first motor rotatably drives the drum magazine to rotate the drum magazine relative to the housing,
    and wherein the drum magazine defines a plurality of the chambers with one or more of the plurality of the chambers containing an analytic consumable therein.

8. The handheld analysis device of claim 6 wherein the drum magazine defines a removal opening at one end of the chamber,
    and wherein the pushrod forces, when moved, the analytic consumable at least partially out of the chamber of the drum magazine via the removal opening.

9. The handheld analysis device of claim 8 wherein the drum magazine has a front face defining the removal opening,
    and wherein the drivable conveyance roll is situated directly adjacent to the front face of the drum magazine.

10. The handheld analysis device of claim 8 wherein the drum magazine defines an insertion opening diametrically opposite the removal opening,
    and wherein the pushrod extends, when moved, into the insertion opening to force the analytic consumable at least partially out of the removal opening of the drum magazine.

11. The handheld analysis device of claim 10 further comprising a drive that drives the drivable conveyance roll.

12. The handheld analysis device of claim 11 wherein the drive comprises a threaded rod defining a thread that extends laterally along the drum magazine, the threaded rod cooperating together with a shaft to drive the drivable conveyance roll.

13. The handheld analysis device of claim 12 wherein the drive further comprises a transmission that cooperates together with the threaded rod via a gearwheel to move the movable pushrod.

14. The handheld analysis device of claim 11 wherein the drive and the drivable conveyance roll cooperate to reintroduce the analytic consumable into the drum magazine after analysis of the sample received on the analytic consumable.

15. The handheld analysis device of claim 3 wherein the drivable conveyance roll defines a geometrical longitudinal axis and is drivable along its geometrical longitudinal axis both clockwise and counterclockwise in order to move the gripped analytic consumable toward the housing opening and away from the housing opening.

16. The handheld analysis device of claim 1 further comprising a counter roll,
wherein a conveyance gap is defined between the drivable conveyance roll and the counter roll through which the analytic consumable is moved.

17. The handheld analysis device of claim 16 wherein the conveyance gap has a profile tailored to the analytic consumable.

18. The handheld analysis device of claim 1 further comprising a conveyance surface that is stationary relative to the drivable conveyance roll,
wherein a conveyance gap is defined between the drivable conveyance roll and the conveyance surface through which the analytic consumable is moved.

19. The handheld analysis device of claim 18 wherein the conveyance gap has a profile tailored to the analytic consumable.

20. The handheld analysis device of claim 3 further comprising an additional drivable conveyance roll for removing the analytic consumable from the housing via the housing opening, the drivable conveyance roll and the additional drivable conveyance roll being situated at a distance from one another along the conveyance path.

21. The handheld analysis device of claim 1 further comprising a display unit configured to display a result of an analysis of the sample.

22. The handheld analysis device of claim 1 wherein the sample is a biological liquid.

* * * * *